(12) United States Patent
Kang et al.

(10) Patent No.: US 9,243,887 B2
(45) Date of Patent: Jan. 26, 2016

(54) LATERAL DISTORTION CORRECTED OPTICAL COHERENCE TOMOGRAPHY SYSTEM

(71) Applicant: The Johns Hopkins University, Baltimore, MD (US)

(72) Inventors: Jin U. Kang, Ellicott City, MD (US); Xuan Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 182 days.

(21) Appl. No.: 13/734,715

(22) Filed: Jan. 4, 2013

(65) Prior Publication Data

US 2013/0188196 A1 Jul. 25, 2013

Related U.S. Application Data

(60) Provisional application No. 61/583,020, filed on Jan. 4, 2012.

(51) Int. Cl.
*G01B 9/02* (2006.01)
*A61B 5/00* (2006.01)

(52) U.S. Cl.
CPC .......... *G01B 9/02091* (2013.01); *G01B 9/0207* (2013.01); *G01B 9/02044* (2013.01); *G01B 9/02072* (2013.01); *A61B 5/0066* (2013.01); *G01B 2290/65* (2013.01)

(58) Field of Classification Search
CPC ........... G01B 9/02044; G01B 9/02091; G01B 9/02087; G01B 9/02085; G01B 9/02076
See application file for complete search history.

(56) References Cited

U.S. PATENT DOCUMENTS

2011/0058175 A1 3/2011 Suehira
2011/0275931 A1 11/2011 Debuc

FOREIGN PATENT DOCUMENTS

| JP | 2008-528954 A | 7/2008 |
| JP | 2008-194106 A | 8/2008 |
| JP | 2011-019576 A | 2/2011 |

OTHER PUBLICATIONS

W. Luo, D. L. Marks, T. S. Ralston, and S. A. Boppart, "Three-dimensional optical coherence tomography of the embryonic murine cardiovascular system," J. Biomed. Opt 11, 021014-021018 (2006).*
Ahmad et al., "Cross-correlation-based image acquisition technique for manually-scanned optical coherence tomography," *Opt. Express* 17, 8125-8136 (2009).

(Continued)

*Primary Examiner* — Hwa Lee
(74) *Attorney, Agent, or Firm* — Venable LLP; Henry J. Daley; Laura G. Remus

(57) ABSTRACT

A lateral-distortion corrected optical coherence tomography system. The system can include an optical coherence tomography sensor, a light source, a fiber-optic system arranged to provide a reference beam and an observation beam, an optical detection system arranged to receive combined light from the reference beam and the observation beam and to provide detection signals, and a data processing system arranged to communicate with the optical detection system and receive the detection signals. The data processing system can be configured to assemble an image corresponding to a scanning path by constructing a plurality of A-scans from the detection signals, determining displacement information from the plurality of A-scans, and arranging the plurality of A-scans according to the displacement information.

12 Claims, 10 Drawing Sheets

(56) References Cited

OTHER PUBLICATIONS

Balicki et al., "Single fiber optical coherence tomography microsurgical instruments for computer and robot-assisted retinal surgery," *Proceedings of the MICCAI Conference*, London, 108-115 (2009).

Barton et al., "Flow measurement without phase information in optical coherence tomography images," *Opt. Express* 13, 5234-5239 (2005).

Boppart et al., "Forward-imaging instruments for optical coherence tomography," *Opt. Lett.* 22, 1618-1620 (1997).

Chen et al., "Determination of scan-plane motion using speckle decorrelation: Theoretical considerations and initial test," *Int J Imaging Syst Technol* 8, 38-44 (1997).

Han et al., "Common-path Fourier-domain optical coherence tomography with a fiber optic probe integrated Into a surgical needle," *Proceedings of CLEO Conference* (2009).

Han et al., "Handheld forward-imaging needle endoscope for ophthalmic optical coherence tomography inspection," *J. Biomed. Opt* 13, 020505 (2008).

Huang et al., "Optical coherence tomography," *Science* 254, 1178-1181 (1991).

Huo et al., "Forward-viewing resonant fiber-optic scanning endoscope of appropriate scanning speed for 3D OCT imaging," *Opt. Express* 18, 14375-14384 (Jun. 2010).

Jung et al., "Three-dimensional optical coherence tomography employing a 2-axis microelectromechanical scanning mirror," *IEEE J. Sel. Top. Quantum Electron.* 11, 806-810 (2005).

Kang et al., "Endoscopic functional Fourier domain common path optical coherence tomography for microsurgery," *IEEE J. of Select. Topic in Quantum. Electron.* 16, 781-792 (Jul./Aug. 2010).

Lau et al., "Imaging true 3D endoscopic anatomy by incorporating magnetic tracking with optical coherence tomography: proof-of-principle for airways," *Opt. Express* 18, 27173-27180 (Dec. 2010).

Lee et al., "Motion correction for phase-resolved dynamic optical coherence tomography imaging of rodent cerebral cortex," *Opt. Express* 19, 21258-21270 (Oct. 2011).

Li et al., "Imaging needle for optical coherence tomography," *Opt. Lett.* 25, 1520-1522 (2000).

Li et al., "On velocity estimation using speckle decorrelation," *IEEE Trans. Ultrason. Ferroelectr. Freq. Control* 48, 1084-1091 (2001).

Li et al., "SNR Analysis of all-fiber common-path optical coherence tomography," *Appl. Opt.* 47, 4833-4840 (2008).

Liu et al., "Progress toward inexpensive endoscopic high-resolution common-path OCT", *Proc. SPIE* 7559, 755902 (2010).

Liu et al., "Deconvolution methods for image deblurring in optical coherence tomography," *J. Opt. Soc. Am. A* 26, 72-77 (2009).

Ren et al., "Manual-scanning optical coherence tomography probe based on position tracking," *Opt. Lett.* 34, 3400-3402 (2009).

Schmitt et al., "Speckle in optical coherence tomography," *J. Biomed. Opt.* 4, 95-105 (1999).

Singh et al., "Physiological tremor amplitude during retinal microsurgery," *Proc. 28th IEEE Northeast Bioeng. Conf*, 171-172 (2002).

Wagner et al., "Statistical properties of radio-frequency and envelope-detected signals with applications to medical ultrasound," J. Opt. Soc. Am. A 4, 910-922 (1987).

Woolliams et al., "Spatially deconvolved optical coherence tomography," Appl. Opt.49(11), 2014-2021 (Apr. 2010).

Wu et al., "Paried-angle-rotation scanning optical coherence tomography forward-imaging probe," *Opt. Lett*.31, 1265-1267 (2006).

Zhang et al., "A surface topology and motion compensation system for microsurgery guidance and intervention based on common-path optical coherence tomography," IEEE Trans. Biomed. Eng. 56(9), 2318-2321 (2009).

Zhang et al., "Graphics processing unit accelerated non-uniform fast Fourier transform for ultrahigh-speed, real-time Fourier-domain OCT," Opt. Express 18, 23472-23487 (Oct. 2010).

Zysk et al., "Optical coherence tomography: a review of clinical development from bench to bedside," J. Biomed. Opt 12, 051403-051421 (2007).

\* cited by examiner

LATERAL DISTORTION CORRECTED OPTICAL COHERENCE TOMOGRAPHY SYSTEM

CROSS REFERENCE TO RELATED APPLICATION

This application claims the benefit of U.S. Provisional Application No. 61/583,020, titled "Distortion-free, free-hand OCT imaging," which was filed Jan. 4, 2012.

FEDERAL FUNDING

This invention was made with Government support of Grants Number NIH, 1R01 EB 007969-01; NIH, NINDS 1R21NS063131-01A1; and NIH/NIE R01 1R01EY021540-01A1, awarded by the Department of Health and Human Services, National Institutes of Health (NIH). The U.S. Government has certain rights in this invention.

BACKGROUND

1. Field of Invention

The field of the currently claimed embodiments of this invention relates to optical coherence tomography, and more particularly to scanning speed variance correction in optical coherence tomography.

2. Discussion of Related Art

Optical coherence tomography (OCT) is a high resolution optical imaging modality widely used in biological and medical fields [1, 2]. For many clinical or intraoperative applications, a hand-held OCT system could be particularly useful; it would offer physicians greater freedom to access imaging sites of interest [3-10]. In a hand-held OCT system, it is desirable to have a robust and lightweight probe which can image detailed anatomical structures with a large field-of-view.

In conventional OCT systems, a mechanical scanner steers the OCT probe beam to perform lateral scans. Sequentially acquired A-scans are assembled according to a pre-defined raster [1] or circumferential [10] scanning patterns to form two dimensional (2D) or three dimensional (3D) images. Scanners used for OCT include galvanometer-mounted mirrors, piezoelectric transducers (PZT) and microelectromechanical systems (MEMS). Galvanometers have a high linearity and accuracy; however, they are usually bulky and heavy, especially in the case of 3D imaging which requires two galvanometers to perform 2D transverse scans. PZT scanners are smaller than galvanometers and therefore are more suitable for hand-held probes. However, they require a high driving voltage, which is a safety concern. MEMS scanners are smaller but relatively expensive, and they require relatively high voltage [11].

On the other hand, OCT scans can also be performed manually, similar to manually-scanned ultrasound imaging systems [12, 13]. A manually-scanned OCT probe without any mechanical scanner to steer the beam could be much simpler, cost-effective, and easy to use during intraoperative settings [14]. It has been shown that a simple 1D, hand-held OCT probe integrated with standard surgical instruments can be used for 2D OCT imaging and depth ranging during surgery [8, 15]. When surgeons manually scan the OCT probe integrated with a surgical tool across the target transversally, the time-varying A-scans can be acquired sequentially and can be used to form pseudo B-scan images. Due to the non-constant scanning velocity of the surgeon's hand, such a pseudo B-scan results in a non-uniform spatial sampling rate in lateral dimension. Such artifact varies widely between surgeons depending on the stability and dexterity of their hands.

Researchers in the ultrasound community have developed various methods in the last decade to correct the artifact induced by the non-constant scanning velocity in manual scanning, and ultrasound imaging systems have benefited from the use of manually scanned probes. In addition, methods including position tracking and speckle decorrelation have recently been adopted by the OCT community [9, 14, 16, 17]. The speckle decorrelation algorithm is particularly interesting and was demonstrated a few years ago by A. Ahmad et al. in OCT systems for the first time [14]. Compared to a video position tracking system, the speckle decorrelation technique may achieve better accuracy because the dimension of OCT speckle is in the order of micrometers [18]; which is sufficient for high-resolution OCT with a micrometer-resolution. Speckle decorrelation algorithm is attractive also because it does not require extra hardware components and is easy to implement.

SUMMARY

According to an embodiment of the present invention, a lateral-distortion corrected optical coherence tomography system is disclosed. The system can include an optical coherence tomography sensor, a light source, a fiber-optic system arranged to provide a reference beam and an observation beam, an optical detection system arranged to receive combined light from the reference beam and the observation beam and to provide detection signals, and a data processing system arranged to communicate with the optical detection system and receive the detection signals. The data processing system can be configured to assemble an image corresponding to a scanning path by constructing a plurality of A-scans from the detection signals, determining displacement information from the plurality of A-scans, and arranging the plurality of A-scans according to the displacement information.

According to a further embodiment of the present invention, a method for lateral-distortion correction in optical coherence tomography is disclosed. The method can include receiving optical coherence tomography signals corresponding to a scanning path, constructing a plurality of A-scans from the optical coherence tomography signals, determining displacement information from the plurality of A-scans, arranging the plurality of A-scans according to the displacement information; and assembling an image corresponding to a scanning path.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
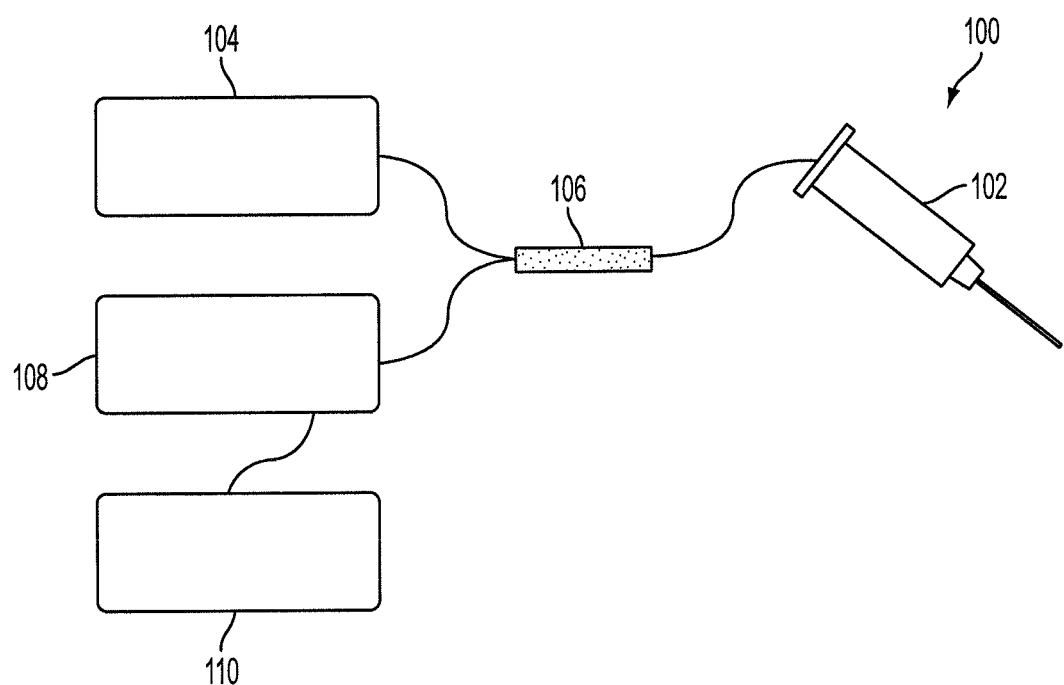
FIG. 1 shows an OCT system with scanning speed variance correction according to an embodiment of the current invention.

FIG. 1 provides a schematic illustration of a lateral-distortion corrected optical coherence tomography system 100 according to an embodiment of the current invention. Lateral-distortion corrected optical coherence tomography system 100 can be any type of optical coherence tomography system as desired. In some embodiments, lateral-distortion corrected optical coherence tomography system 100 can be a spatially encoded frequency domain OCT, a time encoded frequency domain OCT, a time domain OCT, or any other type of OCT as desired.

Lateral-distortion corrected optical coherence tomography system 100 includes an optical coherence tomography sensor 102. Optical coherence tomography sensor 102 can be a mechanical scanner, a handheld sensor or probe, or any other type of sensor as desired.

Lateral-distortion corrected optical coherence tomography system 100 includes a light source 104. The terms "light" or "optical" as used herein are intended to have a broad meaning that can include both visible and non-visible regions of the electromagnetic spectrum. For example, visible, near infrared, infrared and ultraviolet light are all considered as being within the broad definition of the term "light." Light source 104 can provide any type of light as desired. In some embodiments, light source 104 can be, for example, a superluminescent (SLED) light source.

Lateral-distortion corrected optical coherence tomography system 100 includes a fiber optic system 106. Fiber optic system 106 can be optically coupled to light source 104 and said optical coherence tomography sensor 102, and can be arranged or otherwise configured to provide a reference beam and an observation beam. FIG. 1 shows an example of an embodiment in which the observation beam and the reference beam are provided along the same fiber optic path to optical coherence tomography sensor 102. In other embodiments, the observation beam and the reference beam can be provided along separate fiber optic paths within fiber optic system 106.

Lateral-distortion corrected optical coherence tomography system 100 also includes optical detection system 108. Optical detection system 108 can be arranged or otherwise configured to receive combined light from the reference beam and observation beam of fiber optic system 106. Optical detection system 108 can also provide detection signals based on the combined light received from fiber optic system 106.

In some embodiments, the lateral-distortion corrected optical coherence tomography system 100 further includes a data processing system 110 configured to receive detection signals from optical detection system 108 and generate the any type of image, for example optical coherence tomography A-scans, images constructed from a plurality of optical coherence tomography A-scans, or any other type of image as desired. The data processing system 110 can be a workstation, for example. However, the broad concepts of the current invention are not limited to this example. Other data processing systems could be used according to the particular application. For example, the data processing system could be an application specific system, such as, but not limited to one or more ASICs and/or FPGAs. The data processing system could also be a personal computer, a laptop computer, a tablet computer, etc. It could also be a local or distributed computer, such as a computing system distributed over a local or wide area network, including the internet. The data processing system can also include one or more CPUs for running software and/or one or more graphics processing units (GPUs).

In some embodiments, the data processing system 110 can be further configured to perform correction of errors contained in the detection signals. For example, in some embodiments, data processing system 110 can collect a plurality of A-scans. The displacement between adjacent A-scans within this plurality of A-scans can be non-uniform due to variance in the scanning speed of optical coherence tomography sensor 102. Data processing system 110 can use, for example, a correlation between each adjacent A-scan to calculate a displacement estimate between each adjacent A-scan. Data processing system 110 can use this plurality of A-scans and the calculated displacement estimates to assemble an accurate image that does not contain, for example, artifacts, distortions, or other errors caused by variance in the scanning speed of optical coherence tomography sensor 102.

In some embodiments, Data processing system 110 can do this by arranging each A-scan into an image according to the displacement estimates. For example, each A-scan in the plurality of A-scans can be placed in a relative position in an image that is determined by the displacement estimates.

In further embodiments, Data processing system 110 can do produce an accurate image by first adding the displacement estimates together in order to determine a total displacement over the entire plurality of A-scans. Data processing 110 can then divide the total displacement into spatial positions that have a uniform displacement, and interpolate the A-scan data from the original plurality of A-scans at these spatial positions using the displacement estimates. In this way, data processing system 110 can construct a new plurality of A-scans in which the displacement between adjacent A-scans is uniform, and then use this new plurality of A-scans to assemble an image that is free from artifacts or other distortions due to scanning speed variance.

Further additional concepts and embodiments of the current invention will be described by way of the following examples. However, the broad concepts of the current invention are not limited to these particular examples.

EXAMPLES

In this example, we incorporated the theoretical speckle model into the decorrelation function to explicitly correlate the cross-correlation coefficient (XCC) to the lateral displacement between adjacent A-scans. We performed a series of experimental calibrations to validate our model and to show that lateral displacement between adjacent A-scans can be extracted quantitatively based on XCC. With the displacement extracted, we were able to correct the artifact induced by the non-constant scanning velocity. To test the method, we built and demonstrated a freehand-scanning OCT system capable of real-time scanning speed correction—for the first time to the best of our knowledge. Our system consists of a simple hand-held probe, a spectral-domain OCT engine, and software for image reconstruction and scanning speed correction. We integrated a single-mode fiber with a needle to serve as our probe. The spectral domain OCT engine uses a line scan CCD camera for spectral interferogram acquisition. We also developed our high speed software for real-time signal processing based on a general-purpose graphic processing unit (GPGPU). To demonstrate the system, using a simple 22 gauge needle integrated with a single-mode fiber probe, we obtained OCT images from various samples by freehand manual scanning, including images obtained from human in vivo.

One significant difference between this example and Ref [14] is that our method can directly calculate lateral displacement from the value of cross-correlation coefficient based on the speckle model we derived. Moreover, in this example, we have developed real-time scanning speed correction algorithm, because the scanning speed correction algorithm proposed in the manuscript could be easily parallelized and implemented using GPGPU Theory In this example, we use a Cartesian coordinate system (x, y, z) to describe the 3D space. z indicates the axial direction; x is the lateral direction or the direction of the manual scan. For simplicity, we assume the motion of the OCT needle probe is limited to x-z plane and the specimen is static.

Manually Scanned OCT Imaging

Figure 2:
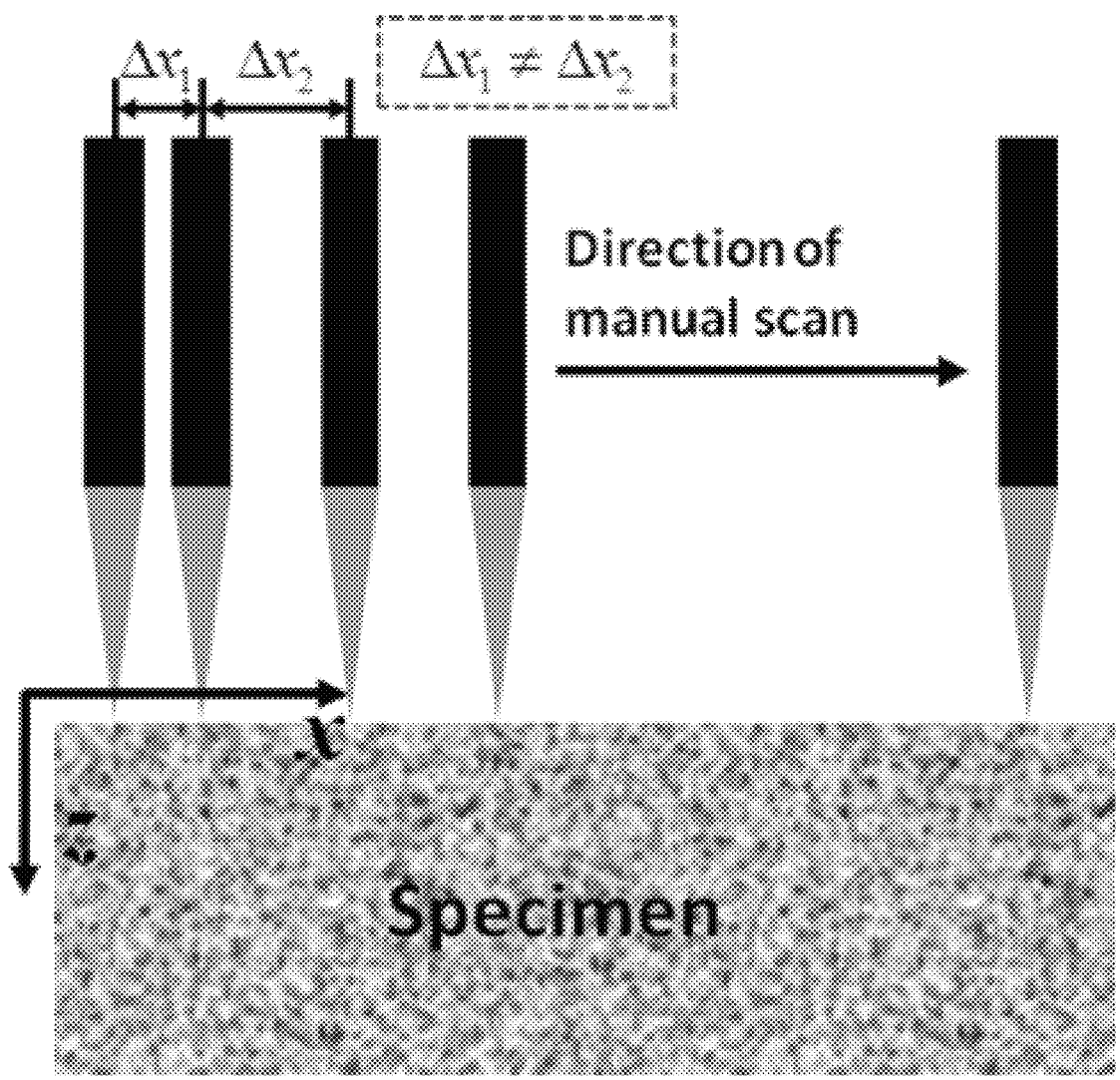
FIG. 2 shows a schematic of manual-scanned OCT imaging with time-varying scanning speed according to an embodiment of the current invention.

As shown in FIG. 2. when a simple hand-held OCT probe without mechanical scanner is scanned manually in x direction, the displacement between adjacent A-scans, $\Delta x$, is a function of the instantaneous scanning velocity v and the A-scan acquisition rate $f_A$, as shown in Eq (1).

$$\Delta x = \frac{v}{f_A} \quad (1)$$

v varies with time for a manual-scan OCT probe; $f_A$ is usually a constant for conventional data acquisition devices such as a frame grabber synchronized with an internal, periodical trigger signal. As a result, $\Delta x$ varies with time in the same manner as v. Therefore, the lateral intervals between different A-scans are different for manual scan.

According to Nyquist theorem, the sampling rate, R, has to be larger than twice the highest spatial frequency of the specimen ($F_n$): $R = 1/\Delta x = f_A/v > 2F_n$. Therefore, the scanning speed has to be smaller than $v_m$ shown in Eq (2).

$$v_m = \frac{f_A}{2F_n} \quad (2)$$

Eq (2) also implies that a scanning velocity smaller than $v_m$ would lead to oversampling and information redundancy. Under the oversampling condition, there is correlation between adjacent A-scans. The degree of correlation can be measured by Pearson cross-correlation coefficient (XCC) shown as Eq (3).

$$\rho_{I_{x,y}(z), I_{x+\Delta x, y+\Delta y}(z+\Delta z)} = \frac{\langle [I_{x,y}(z) - \langle I_{x,y}(z) \rangle][I_{x+\Delta x, y+\Delta y}(z+\Delta z) - \langle I_{x,\Delta x, y+\Delta y}(z+\Delta z) \rangle] \rangle}{\sigma_{I_{x,y}(z)} \sigma_{I_{x+\Delta x, y+\Delta y}(z+\Delta z)}} \quad (3)$$

In Eq (3), $\langle \ \rangle$ indicates to take the mean value of a signal. Here $I_{x,y}(z)$ is the intensity of an A-scan at (x,y). $I_{x,y}(z)$ is calculated by taking the square of the amplitude of the A-scan. Denote the complex valued OCT signal as $S_{x,y}(z)$; then $I_{x,y}(z) = S_{x,y}(z) S^*_{x,y}(z)$. Similarly, $I_{x+\Delta x, y+\Delta y}(z+\Delta z)$ is the intensity of A-scan that is displaced by ($\Delta x$, $\Delta y$, $\Delta z$). $\sigma_{I_{x,y}(z)}$ and $\sigma_{I_{x+\Delta x, y+\Delta y}(z+\Delta z)}$ are the square roots of variance for $I_{x,y}(z)$ and $I_{x+\Delta x, y+\Delta y}(z+\Delta z)$.

As we assume the scanning is in x direction, $\Delta y = \Delta z = 0$, $I_{x+\Delta x, y+\Delta y}(z+\Delta z)$ becomes $I_{x+\Delta x, y}(z)$ and Eq (3) becomes:

$$\rho_{I_{x,y}(z), I_{x+\Delta x, y}(z)} = \frac{\langle [I_{x,y}(z) - \langle I_{x,y}(z) \rangle][I_{x+\Delta x, y}(z) - \langle I_{x, \Delta x, y}(z) \rangle] \rangle}{\sigma_{I_{x,y}(z)} \sigma_{I_{x+\Delta x, y}(z)}}$$

For simplicity, we use $\rho$ to denote $\rho_{I_{x,y}(z), I_{x+\Delta x, y}(z)}$ in subsequent equations.

If we assume the specimen has a homogeneous distribution of scatterers with a uniform scattering strength [19], e.g., the speckle is fully developed, the following relationship exist: $\langle I_{x,y}(z) \rangle = \langle I_{x+\Delta x, y}(z) \rangle = I_0$; $\langle I_{x,y}(z)^2 \rangle = \langle I_{x+\Delta x, y}(z)^2 \rangle = I_{RMS}^2$. Therefore, we have:

$$\sigma_{I_{x,y}(z)}^2 = \langle [I_{x,y}(z) - \langle I_{x,y}(z) \rangle]^2 \rangle = \langle I_{x,y}(z)^2 \rangle - \langle I_{x,y}(z) \rangle^2 = I_{RMS}^2 - I_0^2$$

$$\sigma_{I_{x+\Delta x, y}(z)}^2 = \langle [I_{x+\Delta x, y}(z) - \langle I_{x+\Delta x, y}(z) \rangle]^2 \rangle = \langle I_{x+\Delta x, y}(z)^2 \rangle - \langle I_{x+\Delta x, y}(z) \rangle^2 = I_{RMS}^2 - I_0^2$$

$$\langle [I_{x,y}(z) - \langle I_{x,y}(z) \rangle][I_{x+\Delta x, y}(z) - \langle I_{x+\Delta x, y}(z) \rangle] \rangle = \langle I_{x,y}(z) I_{x+\Delta x, y}(z) \rangle - I_0^2$$

Based on the above relationships, we can simplify Eq. (3) to:

$$\rho = \frac{\langle I_{x,y}(z) I_{x+\Delta x,y}(z)\rangle - I_0^2}{I_{RMS}^2 - I_0^2}$$

Similar to ultrasound images with fully developed speckle, with the moment theorem for the jointly zero mean, Gaussian random variables, and assuming that the real and imaginary parts of S are uncorrelated, we have, $$\langle I_{x,y}(z) I_{x+\Delta x,y}(z)\rangle = |\langle S_{x,y}(z) S_{x+\Delta x,y}^*(z)\rangle|^2 + I_0^2 \quad (4)$$

It is worth mentioning that to derive Eq (4), we only utilized statistical properties of the random variable involved. On the other hand, such statistical property is not related to the physical mechanisms of OCT image formation; and therefore the Eq (4) is applicable to OCT signal.

In the Eq. (4), $|\cdot|^2$ is the square of the amplitude of a complex value. Signal $S_{x,y}(z)$ is determined by the physics of OCT image formation mechanism and can be expressed as the convolution of scattering distribution function $a(x,y,z)$ with system's 3D point spread function (PSF) $P(x,y,z)$ $$S_{x,y}(z) = \iiint_{x',y',z'} a(x-x', y-y', z-z') P(x', y', z') dx' dy' dz'$$

Similarly, OCT signal $S_{x+\Delta x,y}(z)$ can be expressed as $$S_{x+\Delta x,y}(z) = \iiint_{x',y',z'} a(x+\Delta x-x', y-y', z-z') P(x', y', z') dx' dy' dz'$$

It is worth mentioning that $\int$ indicates integration over $(-\infty, +\infty)$ in the expressions of $S_{x,y}(z)$, $S_{x+\Delta x,y}(z)$ and in the following derivations.

Plugging the expression of $S_{x,y}(z)$ and $S_{x+\Delta x,y}(z)$ into Eq (4) and utilizing the fact that OCT system's PSF is not random, we have:

$$\langle I_{x,y}(z) I_{x+\Delta x,y}(z)\rangle =$$

$$\left| \iiint_{x',y',z'} \iiint_{x'',y'',z''} \left( a\begin{pmatrix} x-x', \\ y-y', \\ z-z' \end{pmatrix} a\begin{pmatrix} x+\Delta x-x'', \\ y-y'', \\ z-z'' \end{pmatrix} \right) \right|^2 + I_0^2$$

$$P(x', y', z') P^*(x'', y'', z'') dx' dy' dz' dx'' dy'' dz''$$

Assuming that the speckle is fully developed and thus scatterers in different spatial location are described by identical but independent random variables, we have the following relationship:

$$\langle a(x-x',y-y',z-z') a(x+\Delta x-x'',y-y'',z-z'')\rangle = a_0^2 \delta(x'+\Delta x - x'') \delta(y'-y'') \delta(z'-z'')$$

In the above equation, $a_0$ is a constant representing the scattering strength. Using the sifting property of delta function, we have $$\langle I_{x,y}(z) I_{x+\Delta x,y}(z)\rangle =$$

$$\left| \iiint_{x',y',z'} \iiint_{x'',y'',z''} a_0^2 \delta(x'+\Delta x-x'') \delta(y''-y') \delta(z''-z') P(x',y',z') \right.$$
$$\left. P^*(x'',y'',z'') dx' dy' dz' dx'' dy'' dz'' \right|^2 +$$

$$I_0^2 = \left| \iiint_{x',y',z'} a_0^2 P(x',y',z') P^*(x'+\Delta x, y', z') dx' dy' dz' \right|^2 + I_0^2$$

In OCT, the axial PSF $P(z)$ and the lateral PSF $P(x,y)$ are separable because axial and lateral PSFs are governed by different physical principles: axial PSF is determined by the temporal coherence of the light source while lateral PSF is determined by the imaging optics in the sample arm. Furthermore, in Gaussian optics model, $P(x,y)$ is the product of PSFs in x and y dimensions. As a result, $P(x,y,z)$ can be written explicitly as $P(x,y,z) = P_x(x) P_y(y) P_z(z)$ and therefore we have:

$$\langle I_{x,y}(z) I_{x+\Delta x,y}(z)\rangle - I_0^2 = \quad (5)$$

$$\left| a_0^2 \iiint \begin{array}{c} P_x(x') P_y(y') P_z(z') P_x^* \\ (x'+\Delta x) P_y^*(y') P_z^*(z') dx' dy' dz' \end{array} \right|^2 + I_0^2 - I_0^2 =$$

$$\left| \begin{array}{c} a_0^2 \left[ \int_{-\infty}^{+\infty} P_x(x') P_x^*(x'+\Delta x) dx' \right] \\ \left[ \int_{-\infty}^{+\infty} P_y(y') P_y^*(y') dy' \right] \left[ \int_{-\infty}^{+\infty} P_z(z') P_z^*(z') dz' \right] \end{array} \right|^2 =$$

$$\left| a_0^2 \int_{-\infty}^{+\infty} P_y(y') P_y^*(y') dy' \right|^2 \left| \int_{-\infty}^{+\infty} P_z(z') P_z^*(z') dz' \right|^2$$

$$\left| \int_{-\infty}^{+\infty} P_x(x') P_x^*(x'+\Delta x) dx' \right|^2$$

Lateral PSF $P_x(x)$ can be expressed as:

$$P_x(x) = P_0 \exp\left(-\frac{x^2}{w_0^2}\right) \quad (6)$$

In Eq (6), $w_0$ is the Gaussian beam waist of probing beam. It is worth mentioning that Gaussian beam waist in this definition is the distance from the beam axis where the intensity of OCT signal drops to $1/e$.

Plugging Eq. (5) into Eq (4), we have:

$$\rho = \frac{\left|a_0^2 \int_{-\infty}^{+\infty} P_y(y') P_y^*(y') dy'\right|^2 \left|\int_{-\infty}^{+\infty} P_z(z') P_z^*(z') dz'\right|^2}{\left|a_0^2 \int_{-\infty}^{+\infty} P_y(y') P_y^*(y') dy'\right|^2 \left|\int_{-\infty}^{+\infty} P_z(z') P_z^*(z') dz'\right|^2} \cdot \frac{\left|\int_{-\infty}^{+\infty} P_x(x') P_x^*(x'+\Delta x) dx'\right|^2}{\left|\int_{-\infty}^{+\infty} P_x(x') P_x^*(x') dx'\right|^2} =$$

$$\frac{\left|\int P_x(x') P_x^*(x'+\Delta x) dx'\right|^2}{\left|\int P_x(x') P_x^*(x') dx'\right|^2}$$

Using the expression of $P_x(x)$ shown as Eq. (6), $\rho$ can be re-written as:

$$\rho = \frac{\left|\int\left[P_0^2\exp\left(-\frac{x'^2}{w_0^2}\right)\exp\left(-\frac{(x'+\Delta x)^2}{w_0^2}\right)\right]dx'\right|^2}{\left|\int\left[P_0^2\exp\left(-\frac{x'^2}{w_0^2}\right)\exp\left(-\frac{x'^2}{w_0^2}\right)\right]dx'\right|^2} =$$

$$\frac{\left|\int\exp\left(-\frac{2\left(x'+\frac{\Delta x}{2}\right)^2+\frac{\Delta x^2}{2}}{w_0^2}\right)dx'\right|^2}{\left|\int\exp\left(-2\frac{x'^2}{w_0^2}\right)dx'\right|^2}$$

We are able to calculate the integration of Gaussian function over $(-\infty, +\infty)$:

$$\int_{-\infty}^{+\infty}\exp\left(-2\frac{x'^2}{w_0^2}\right)dx' = \int_{-\infty}^{+\infty}\exp\left(-\frac{2\left(x'+\frac{\Delta x}{2}\right)^2}{w_0^2}\right)dx = \sqrt{\pi/2}\,w_0$$

Therefore, $$\rho = \frac{\left|\exp\left(-\frac{\Delta x^2}{2w_0^2}\right)\int\exp\left(-\frac{2\left(x'+\frac{\Delta x}{2}\right)^2}{w_0^2}\right)dx'\right|^2}{\left|\int\exp\left(-2\frac{x'^2}{w_0^2}\right)dx'\right|^2} = \quad (7)$$

$$\frac{\left|\exp\left(-\frac{\Delta x^2}{2w_0^2}\right)\sqrt{\pi/2}\,w_0\right|^2}{\left|\sqrt{\pi/2}\,w_0\right|^2} = \exp\left[-\frac{(\Delta x)^2}{w_0^2}\right]$$

Eq (7) shows that the value of $\rho$ is merely determined by $\Delta x$ for fully developed speckle; therefore, we can calculate the cross-correlation coefficient $\rho$ between adjacent A-scans and use the value of $\rho$ to derive the time-varying $\Delta x$ as:

$$\Delta x = w_0\sqrt{\ln\left(\frac{1}{\rho}\right)} \quad (8)$$

For digitized sample points in A-scans, $\rho$ can be calculated with Eq (9).

$$\rho_{j,j+1} = \frac{\sum_{i=i_f}^{i_l}(I_{ij}-\langle I_j\rangle)(I_{i(j+1)}-\langle I_{(j+1)}\rangle)}{\sqrt{\left[\sum_{i=i_f}^{i_l}(I_{ij}-\langle I_j\rangle)^2\right]\left[\sum_{i=i_f}^{i_l}(I_{i(j+1)}-\langle I_{(j+1)}\rangle)^2\right]}} \quad (9)$$

In Eq (9), i is the index of pixel in an A-scan and j is the index of A-scan. Segmentation of signal between $i_f$ and $i_l$ is selected to calculate $\rho$. Although Eq (3) and Eq (9) implies that XCC can be either positive or negative, it is unlikely that XCC of two adjacent A-scans has very small or negative value when lateral dimension is highly over-sampled. As demonstrated previously, speckle pattern is formed by convolving random scattering field with OCT system's PSF. Due to the finite dimension of PSF, adjacent A-scans are correlated as long as lateral displacement is small compared to the lateral width of PSF, no matter how sample field is like. However, it is true that XCC can become very small or negative. To deal with this problem, in our software implementation, we took the absolute value of XCC for displacement estimation so that the term inside of logarithm operator is never negative. In addition, we applied thresholding to the value of XCC because small XCC indicates decorrelation between A-scans and thus is not reliable for the displacement assessment. It is also worth mentioning that when XCC turns negative, it does not represent the change of scanning direction.

Scanning Speed Correction Based on Speckle Decorrelation

Figure 3:
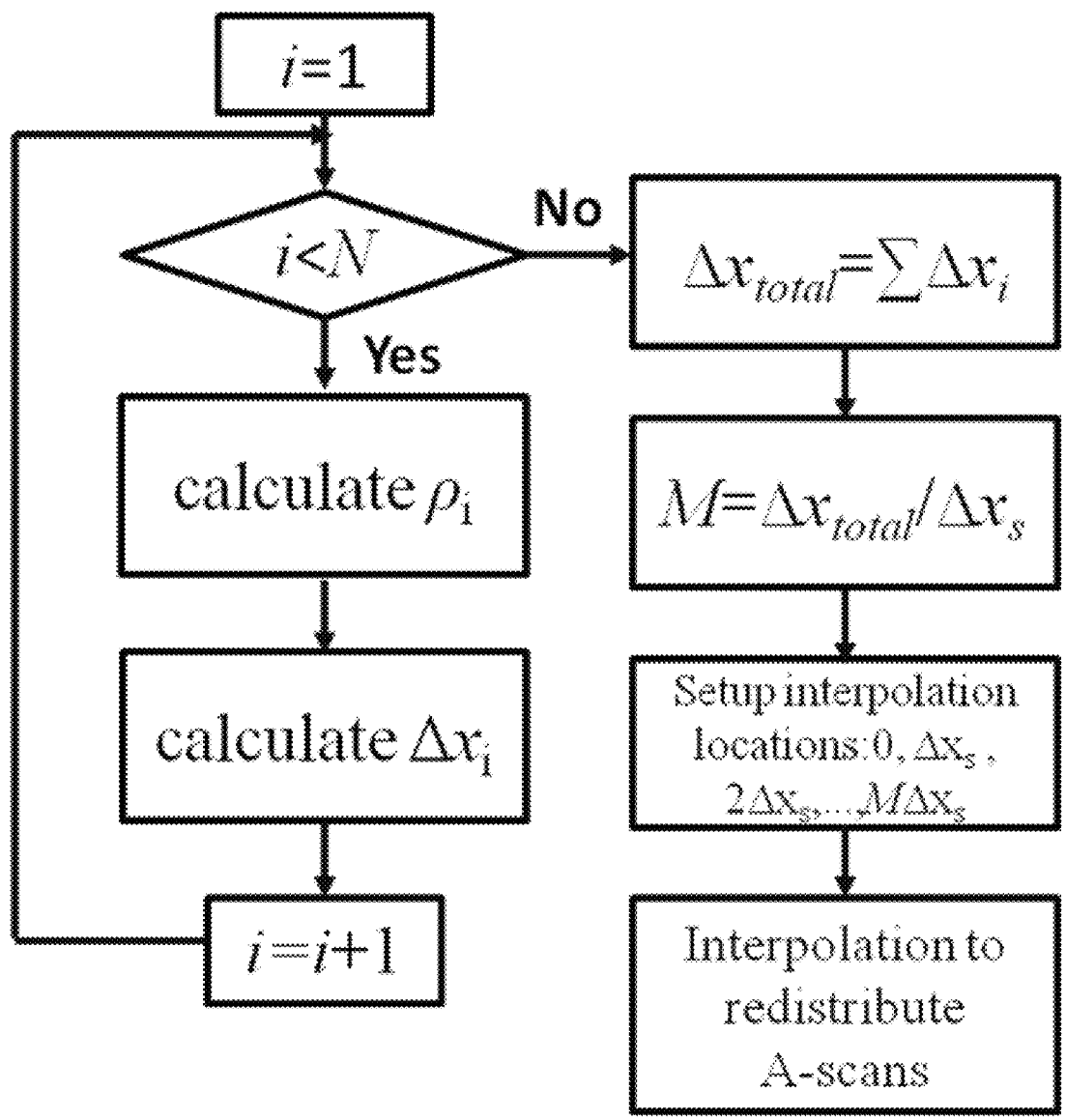
FIG. 3 shows a Flow chart for the scanning speed correction using cross-correlation coefficient according to an embodiment of the current invention.

Eq. (8) indicates that lateral interval between A-scans can be extracted from the XCC and therefore we could use XCC to correct artifact induced by non-constant scanning speed. The flow chart of the scanning speed correction for one frame of data is shown in FIG. 3. In our OCT system, the interferometric spectra are detected by a line scan CCD camera and the data is transferred to the host computer through a frame grabber as frames. One frame consists of N spectra acquired at lateral locations: $x_1, x_2, \ldots, x_N$. Although $\Delta x_i$, the interval between $x_i$ and $x_{i+1}$, is not a constant for different A-scans due to non-constant scanning speed, we could extract $\Delta x_i$ using $\rho_i$, the XCC between $I^*_i(z)$ and $I_{i+1}(z)$ (A-scans obtained at spatial coordinate $x_i$ and $x_{i+1}$). As a result, we were able to estimate $\Delta x_{total}$, the displacement (in x direction) between the first and the last A-scan in a frame by summing up $\Delta x_i$: $\Delta x_{total}=\Sigma\Delta x_i$. With a pre-set sampling interval $\Delta x_s$, we could calculate the number of A-scans required for this particular frame of data by dividing $\Delta x_{total}$ with $\Delta x_s$: $M=\Delta x_{total}/\Delta x_s$. Afterwards, we performed interpolation to obtain A-scan data at spatial points 0, $\Delta x_s$, $2\Delta x_s$, ..., $M\Delta x_s$ to obtain A-scans that were evenly distributed in x dimension.

OCT System and Software Implementation

The basic properties of the OCT system used for our calibration experiments have been reported in our previous work [23]. Briefly, it was a spectral domain OCT system based on GPGPU processing with a 70 kHz A-scan rate. In that set-up, an achromatic doublet lens at the sample arm was used to focus the incident light beam and collect back-scattered photons. We used the focal length of imaging objective, focal length of the collimator, and mode field diameter of the fiber to calculate $w_0$. From our calculation, $w_0$ equaled 6 µm and this indicated a 12 µm 1/e lateral resolution of our OCT. This was further verified by using our OCT system to image 1951 USAF resolution target. The obtained en face OCT image clearly showed that our OCT system can resolve the 5th element in group 6 which corresponds to a 10 µm FWHM lateral resolution and therefore 12 µm 1/e lateral resolution. Therefore, we assumed $w_0$ to be 6 µm for this system when using Eq. (7) to correlate $\rho$ and $\Delta x$. With the 12 µm lateral resolution, $F_n=(1/12)(\mu m^{-1})$; therefore the largest scanning speed that satisfies the requirement of Nyquist sampling is about 420 mm/s, as implied by Eq. (2). For our calibration experiments, a high-speed galvanometer was used to perform lateral scanning.

Figure 4:
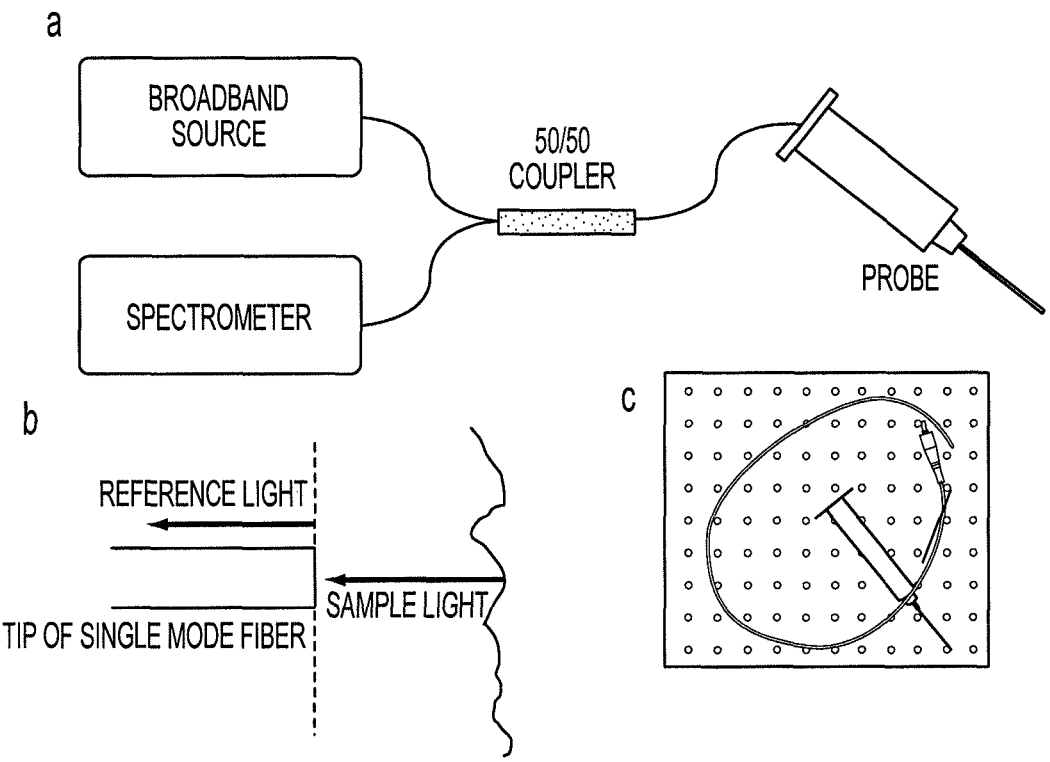
FIGS. 4A-C show (a) a OCT system diagram; (b) a principle of common path interferometer based on single mode fiber; (c) a single mode fiber probe integrated with needle.

Our freehand-scanning OCT was a modified version of this system. As shown in FIG. 4(a), we used a superluminescent diode centered at 840 nm with a full width half maximum bandwidth of 55 nm (Superlum, S840-B-I-20) as a broadband source. The interferometric signals are dispersed spectrally by a spectrometer that consists of a collimator, diffraction grating (Wasatch Photonics, HD 1800 l/mm @ 840 nm), and two identical achromatic doublet lenses (AC508-250-B, f=250 mm) for focusing. The spectra are detected by a line scan CCD camera (e2v, AVIIVA EM4, maximum line rate 70 kHz). Spectral data is transferred through a high-speed frame grabber (Matrox Solios eV-CLF) into our host computer (Dell Precision RS500 Rack Workstation, 6-Core Intel® Xeon® Processor X5690 3.46 GHz, 12 GB RAM, 64 bit Windows 7 operating system). For high-speed signal processing, we implemented massive computation on a GPGPU (Nvidia GeForce GTX 480) with 480 cores, with each core operating at 1.4 GHz. To build a simple, lightweight, and small probe which can have arbitrary length, we adopted a common path (CP) configuration for our interferometer [24, 25]. In the CP interferometer, the reference and sample light shares the same probe arm which is simply a single mode fiber with its tip cleaved in right angle, as in FIG. 4(b). The reference light comes from the Fresnel reflection at the fiber tip. The sample and reference light is routed by a 50/50 fiber optic coupler to the spectrometer. To protect the fragile fiber tip, we integrated the fiber probe with a 22 gauge needle attached to a syringe so that it can be easily hand-held, shown as FIG. 4(c). The system performance was characterized in our previous work [25]. Despite the fact that Gaussian beam diverges, the lateral resolution of our bare fiber probe is higher than 25 μm from results obtained from both experimental measurement and ZEMAX simulation [28].

Figure 5:
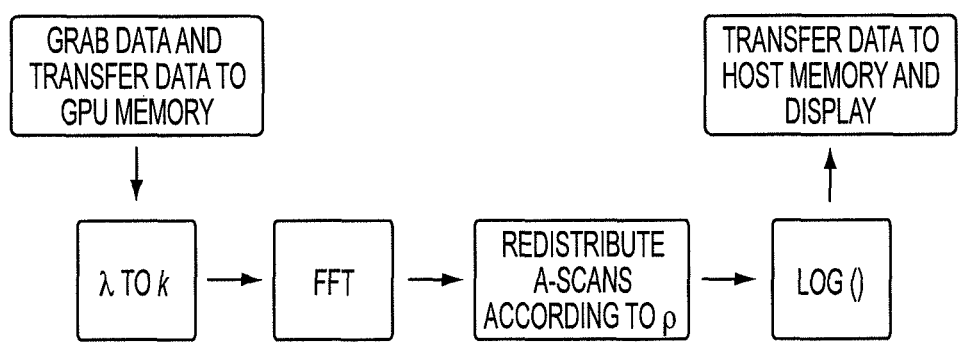
FIG. 5 shows a Block diagram of signal processing for the OCT system with real-time scanning speed variance correction according to an embodiment of the current invention.

The signal processing procedure of our system is briefly summarized in FIG. 5. A data frame containing N spectra was acquired and transferred to GPU memory. Afterwards, we re-sampled the spectral data from wavelength (λ) space to wavenumber (k) space using cubic spline interpolation and then performed fast Fourier transformation (FFT) to obtain A-scans. With the obtained A-scans, we calculated the XCC between adjacent A-scans using the OCT signal intensity and re-distributed the A-scans using algorithm shown in FIG. 3 to achieve uniform spatial sampling. Before calculating ρ, we processed each A-scan with a moving average filter that averages three adjacent pixels in axial direction and subtracted the output of the filter from each A-scan to reduce low spatial frequency components in the A-scan and therefore increase the sensitivity of cross correlation calculation for lateral motion estimate [14]. Due to the high A-scan rate of our OCT system, lateral dimension was highly over-sampled during the manual scan; therefore simple nearest neighbor interpolation could achieve satisfactory result in re-distributing A-scans and achieve uniform lateral sampling. To match the dynamic range of the OCT data and display device, we applied a truncated log transform to the OCT signal before transferring the signal back to the host computer for display. Procedures shown as red blocks in FIG. 5 were implemented with GPU. Moreover, we implemented multi-thread programming so that data acquisition was in parallel with processing; therefore, we were able to acquire spectral data detected by the CCD continuously as long as we kept the data acquisition rate slightly lower than processing rate. Our software is able to process over 62,000 A-scans every second. Although slightly less than the maximum data acquisition rate of our camera (70 k line rate), this speed allows a maximum lateral scanning speed to be approximately 620 mm/s assuming $w_0$ is about 20 μm for the single mode fiber probe and this lateral scanning speed is significantly larger than moderate manual scanning speed (several millimeters per second). With the software optimization, we will be able to further increase the processing speed in future studies.

To obtain an accurate value of $w_0$ in our software for our single mode fiber probe, we have first used an estimation of $w_0$ based on the experimentally measured lateral resolution of our CP OCT system from our previous work [25, 28] and indicate this value as w. Afterwards, we manually scanned a highly scattering phantom for 1 cm (L=1 cm) and acquired a certain number of A-scans that were uniformly distributed. We performed such scanning for 10 times and calculated the average A-scan number in all the measurements which is indicated by M. According to Eq. (8), we were able to obtain a better estimation of $w_0$ that equals (wL)/(M$\Delta x_s$). We varied the value of $\Delta x_s$ and obtained a consistent value of $w_0$. All images in section 5.2 were acquired based on $w_0$=18.5 μm which was constant for different values of $\Delta x_s$.

Calibration of the Relationship Between Cross-Correlation Coefficient and Lateral Displacement In our calibration experiments, we scanned a phantom consisting of 9 layers of cellophane tape to verify the relationship between displacement Δx and ρ (XCC), shown as Eq. (7) and (8). We used a galvanometer to perform lateral scans with known scanning speeds. We applied a periodical sawtooth voltage V from a function generator to the galvanometer and synchronized V with the acquisition of a frame of data which contained N A-scans (N=1000). For a 100% duty cycle sawtooth driving voltage, Δx, lateral interval between adjacent A-scans stays constant because the driving voltage increases linearly during signal acquisition. Therefore, we could calculate the displacement between adjacent A-scans directly from the amplitude of the sawtooth function: Δx=γV/N. Here γ is a coefficient that relates the driving voltage (V) applied to galvanometer and the probing beam displacement (D) at the focal plane of the imaging lens: γ=D/V. γ was measured to be 1.925 mm/V in the OCT setup for our calibration experiments. As a result, by applying different V, we could achieve different scanning speeds and thus different Δx. We acquired B-scans at various scanning speeds. One example of the image obtained is shown 5(a) which contain 1000 A-scans, with a sampling interval Δx equal to 0.96 μm.

Figure 6:
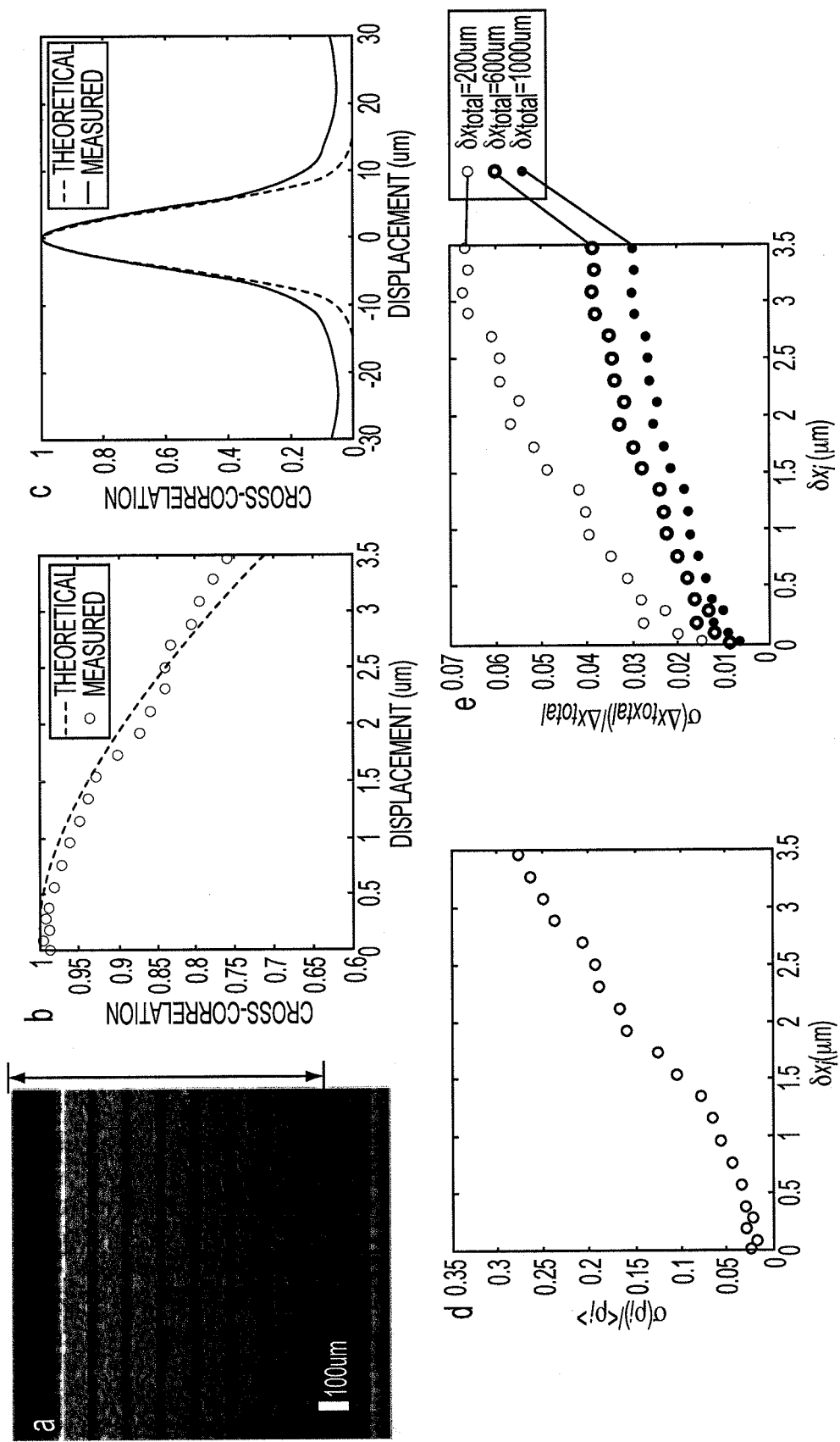
FIGS. 6A-E show (a) an image obtained in calibration experiment ($\Delta x=0.96$ μm); (b) a relationship between $\rho$ and $\Delta x$ obtained by calculating XCC between adjacent A-scans from different B-scans (circles: experimental; dashed line: theoretical); (c) a relationship between $\rho$ and $\Delta x$ obtained by calculating XCC using A-scans with different offsets from the same B-scan (solid line: experimental; dashed line: theoretical); (d) the ratio between standard deviation and mean of $\rho i$, at different sampling intervals; (e) a ratio between $\sigma_{\Delta xtotal}$ and $\Delta x_{total}$.

For B-scan acquired at a certain spatial sampling interval determined by the driving voltage, we calculated $\rho_i$, XCC between the $i^{th}$ and $(i+1)^{th}$ A-scan, using pixels within the range as indicated by the double-head arrow in FIG. 6(a). Afterwards, with all the $\rho_i$ obtained, we took the ensemble average of XCC:

$$\rho = \frac{\left(\sum_{i=1}^{N-1} \rho_i\right)}{(N-1)} \tag{10}$$

Using the above processing, we obtained a value of ρ from each B-scan corresponding to a certain Δx. The result is shown as circles in FIG. 6(b). As a comparison, we also plotted the theoretical relationship between ρ and Δx shown in Eq. (7) as a dashed curve in FIG. 6(b). By calculating ensemble average of XCC using A-scans with different offsets from the same B-scan, we obtained decorrelation curve as shown in FIG. 6(c). Similarly, theoretical relationship between ρ and Δx is shown as a solid curve in FIG. 6(c). The consistency between experimental results and the analytical model described by Eq. (7) and (8) implies that we can use ρ to quantitatively extract the lateral sampling interval and thus correct non-constant scanning speed.

XCC, as the correlation of two random variables, is inherently a random variable. It is very important to evaluate the statistics of XCC to assess the accuracy in displacement estimation. To evaluate the statistics of XCC, we calculated the standard deviation and the mean of $\rho_i$ from B-scans acquired experimentally at different spatial sampling intervals ($\delta x_i$). The results are shown in FIG. 6(d). With each obtained $\rho_i$, we used Eq. (8) to calculate a corresponding displacement value $\Delta x_i$, and then assess the variation of $\Delta x_i$, $\sigma_{xi}^2$. Assume that the displacement between each pair of the A-scans follows the same statistics and the probe travels for a given distance $\Delta x_{total}$. In this case, M, the number of A-scans acquired is $\Delta x_{total}/\delta x_i$. Based on these assumptions, $\sigma_{xtotal}^2$ the variance of the estimated displacement approximately equals $M\sigma_{xi}^2$. In FIG. 6(e), we show the ratio between $\sigma_{\Delta xtotal}$ and $\Delta x_{total}$, for different values of $\Delta x_{total}$ and $\delta x_i$.

As shown in FIG. 6(b) and especially FIG. 6(c), when interval between A-scans is small (<5 μm), the measured XCC values are highly consistent with results from theoretical calculation. However, with larger interval (>5 μm) between A-scans, the measured XCC values become slightly different from the values calculated using Eq (7). Moreover, FIGS. 6(d) and (e) show that a smaller sampling interval (smaller $\delta x_i$) and larger lateral distance travelled would result in a higher accuracy of displacement estimation. In other words, a large number of sampling points for a given displacement can provide a better displacement estimation, due to the inherent statistics of XCC. Other than the random nature of XCC, there are several reasons for displacement calculated using XCC and actual displacement to be different. First, OCT signal suffers from optical and electrical noise, such as shot noise, excess noise, thermal noise, etc; in addition, OCT signal decorrelates overtime due to random environmental disturbance. Second, the waist of probing beam varies at different lateral displacement due to lens abbreviation. Third, parts of A-scans with low signal intensity produced high correlation due to signal absence, so that the measured XCC was higher than the theoretical values for large displacements in FIGS. 6(b) and (c). However, those factors might be negligible as compared to the inherent random noise of XCC, because OCT is a high speed and high sensitivity imaging modality.

Results in FIGS. 6(d) and (e) implies that errors in displacement estimation are minimized with small sampling interval which can vary over time and oversampling in x dimension is necessary for accurate scanning speed correction. Comprehensive evaluation of the error in distance measurement using XCC will be our future work and is beyond of the scope of this manuscript.

Results

Quantitative Lateral Sampling Interval Extraction

We used the same OCT setup for this experiment as in the calibration experiments. To demonstrate that we can use XCC for the quantitative displacement extraction and thus quantitatively correct artifacts from non-uniform scanning speed, we applied a sinusoidal driving voltage (f=28 Hz, Vpp=1.5V) to the galvanometer and scanned the multilayered tape phantom. Knowing voltage applied to galvanometer and the value of γ from our previous measurement, we were able to calculate the displacement of the probe beam with regards to its neutral position when the voltage applied to the galvanometer was 0. The calculated displacement of the probe beam at different time is shown in the upper inset of FIG. 7(a). Instantaneous Δx was calculated by taking the absolute value of the difference between the displacements of adjacent sampling points, as shown in the lower inset of FIG. 7(a). In this experiment, 5000 A-scans were acquired sequentially. By stacking the A-scans, we obtained the pseudo B-scan shown in FIG. 7(b). When the driving voltage/displacement reaches their extreme points, the interval between adjacent A-scans became smallest, which can be clearly seen in FIG. 7(a). With a small sampling interval, data is redundant, as in areas indicated by the arrows in FIG. 7(b). We calculated the XCC between the adjacent A-scans in FIG. 7(b). XCC as a function of time is shown in the upper inset of FIG. 7(c) which was processed with a low pass filter for noise reduction and normalized to the maximum value. We further calculated Δx using Eq. (8) with XCC obtained in the upper inset of FIG. 7(c) and show the result as the labeled curve in the lower inset of FIG. 7(c). In the lower inset of FIG. 7(c), we also plot Δx calculated from the known driving voltage applied to the galvanometer, as the other labeled curve. The consistency between the two curves verified our assumption that Δx could be extracted from XCC quantitatively. There are several reasons for the two curves in the lower inset of FIG. 7(c) to be slightly different, as discussed in the previous section. However, the inherence statistics of XCC plays the most significant role in resulting errors. As shown previously in FIG. 6(d), if the sample is laterally homogenous and the displacement between the adjacent A-scans is small, for example less than 1 μm, the errors in displacement due to the inherent randomness of XCC are small. Therefore, the errors might be mostly due to other random noise in OCT signal. With a larger sampling interval, errors come from the inherent statistics of XCC rather than other noise in OCT signal. As shown in the lower inset of FIG. 7(c), difference between estimated and actual interval is smaller when interval between A-scans is smaller.

Figure 7:
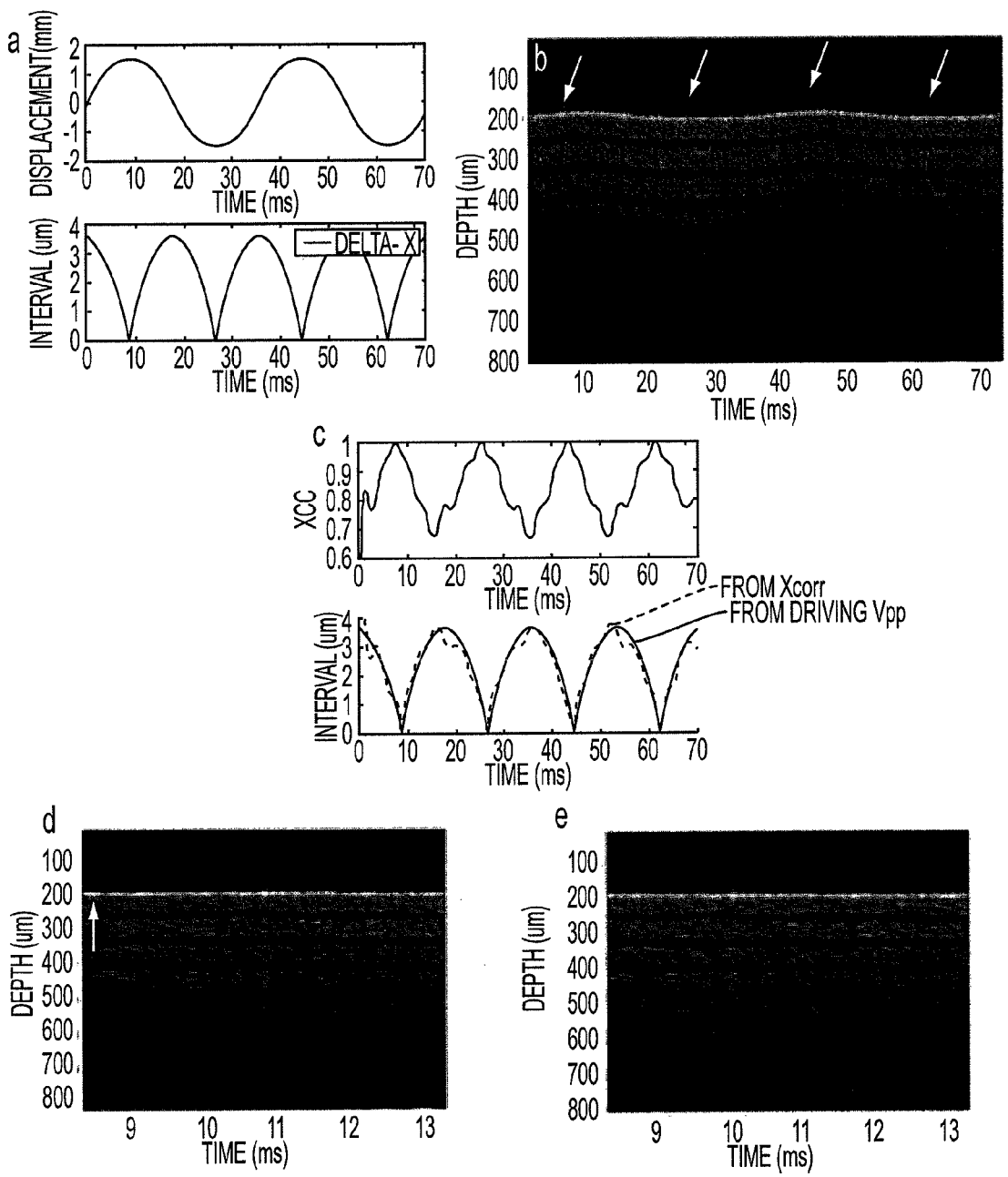
FIGS. 7A-E show (a) displacement of probing beam versus time (upper); $\Delta x$ as a function of time (lower); (b) pseudo B-scan obtained from sinusoidal scanning pattern; (c) upper inset: XCC calculated from adjacent A-scans; lower inset: $\Delta x$ calculated from XCC and ground truth $\Delta x$ calculated from the driving voltage; (d) pseudo B-scan with artifact induced by non-constant scanning speed; (e) B-scan after non-constant scanning speed correction.

To validate the scanning speed correction algorithm, we took A-scans between 8 ms and 13 ms when the scanning velocity did not change its direction; thus, we didn't have to consider the ambiguity of scanning direction. Simply stacking A-scans acquired, we obtained FIG. 7(d) which exhibits an oversampling artifact on the left side of the image, as indicated by the arrow. To remove such artifact, we set sample interval $\Delta x_s$ to be 5 μm and performed nearest neighbor interpolation as described in section 2.2. The resultant image is shown in FIG. 7(e) in which the oversampling artifact is removed.

Figure 8:
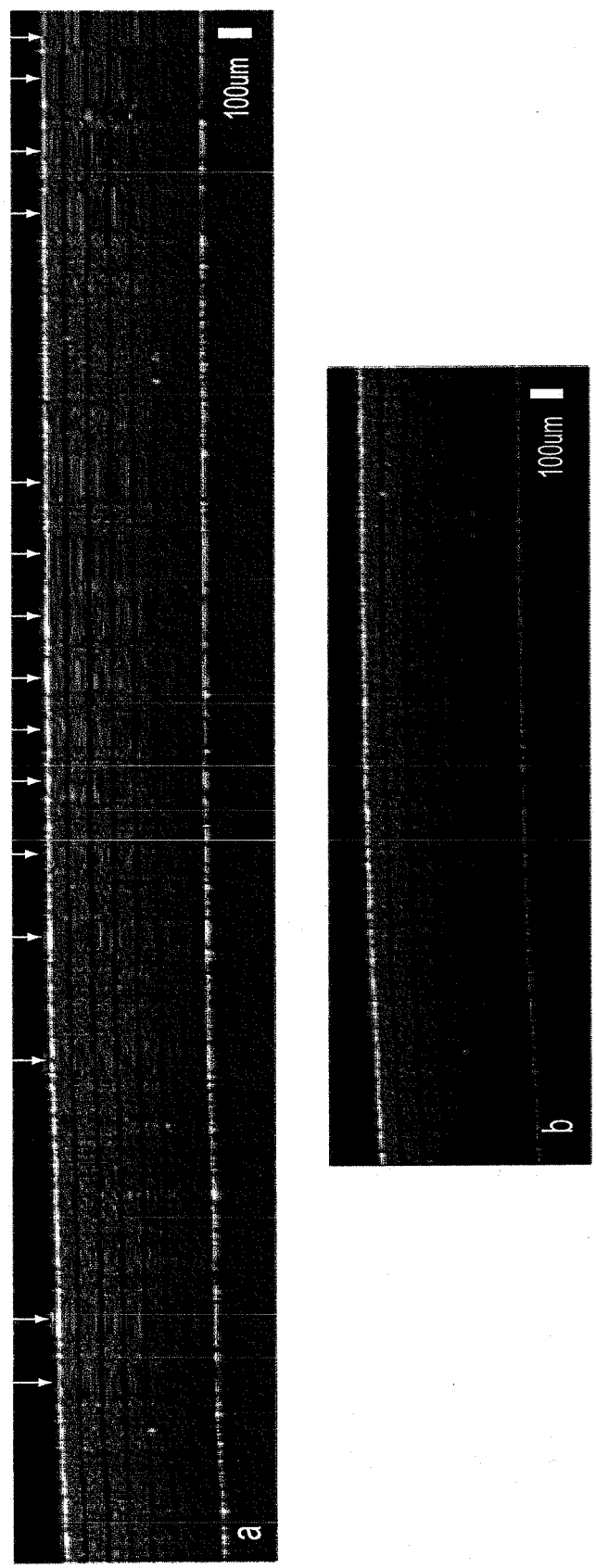
FIGS. 8A-B show OCT images obtained from manual scan: (a) before scanning speed correction; (b) after scanning speed correction. Arrows in FIG. 8(a) indicate areas with motion artifacts.

To demonstrate the effectiveness of our method more clearly, we manually scanned a phantom consisting of multiple layers of tape and saved all the A-scans obtained. Stacking all the A-scans, we obtained FIG. 8(a) which suffers from motion artifacts, as indicated by arrows. After correcting A-scans using the method proposed in this paper, we obtained FIG. 8(b) which is free of distortion due to non-constant scanning speed. It is worth mentioning that scale bars in FIG. 8 are only applicable to axial dimension.

Images Obtained from Manually Scanned OCT Probe with Real-Time Correction

Figure 9:
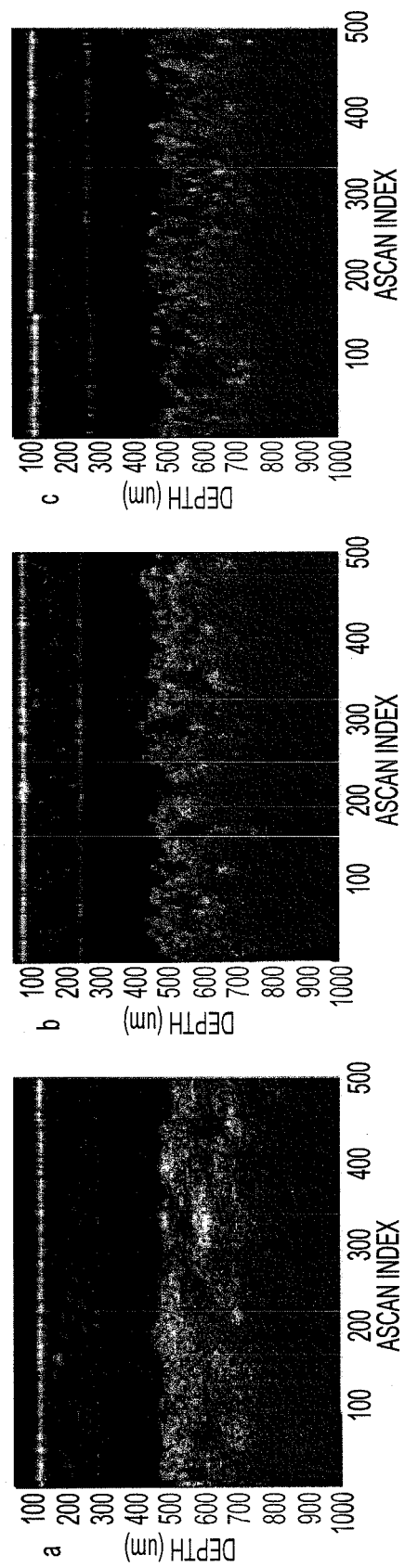
FIGS. 9A-C show Images of IR viewing card with sampling interval $\Delta x_s$ equal to 1 μm (a), 2 μm (b), and 4 μm (c).

Using our scanning speed corrected, hand-held OCT system, we manually scanned our single mode fiber probe across the surface of an infrared (IR) viewing card by moving the probe with a freehand. In our real-time scanning speed correction software, we set the spatial sampling interval $\Delta x_s$ to be 1 μm, 2 μm, and 4 μm and show the corresponding images obtained in FIGS. 9(a), (b), and (c). The plastic covering film and the underneath fluorescence materials of the IR card can be clearly seen from FIG. 9. With different spatial sampling interval $\Delta x_s$, the same physical length is represented by different numbers of A-scans. As the lateral axis of FIG. 9 is A-scan index, the scale of porous structure of the fluorescence materials decreases from FIG. 9(a) to (c) due to the increasing sampling interval. Results in FIG. 9 verify that we were able to achieve uniform spatial sampling interval during manual scan and the sampling interval is explicitly determined through $\Delta x_s$ a which is parameter in our software.

Figure 10:
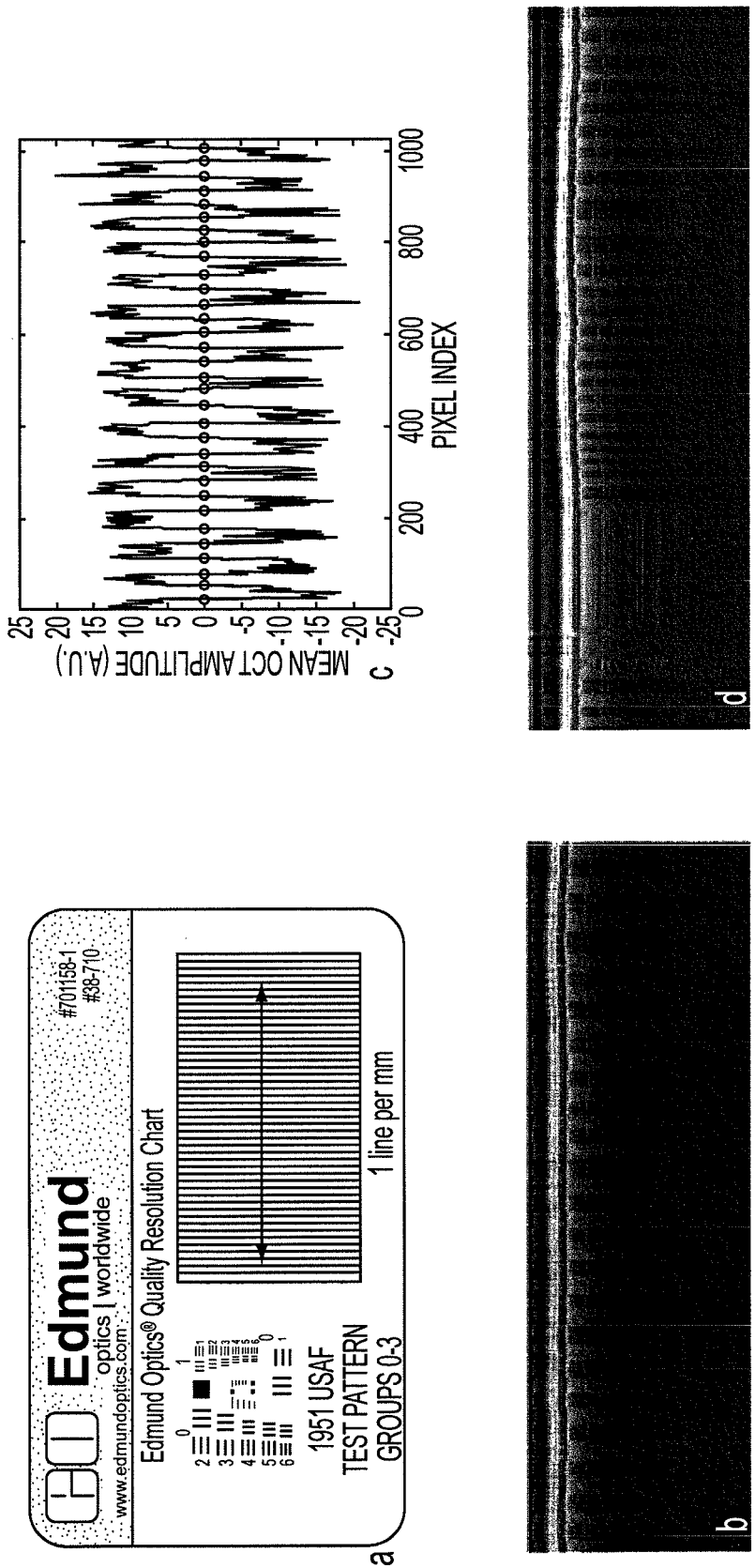
FIGS. 10A-D show (a) photo of quality resolution chart; (b) OCT image obtained from manual scan with scanning speed correction; (c) Mean OCT signal of difference A-scans in FIG. 10(a); zero-crossing points of the curve; (d) OCT image obtained from manual scan without scanning speed correction.

To further evaluate the accuracy of our scanning speed correction method, we imaged a quality resolution chart with 1 line per mm from Edmund Optics through manual scan, as shown in FIG. 10(a). The arrow in FIG. 10(a) indicates the scanning direction. FIG. 10(b) is the image obtained from the software with real-time correction capability. Periodical structure is clearly shown in FIG. 10(b). To quantitatively evaluate the accuracy of our re-sampling algorithm, we averaged signal amplitude of each A-scan in FIG. 10(b), performed mean subtraction and obtained the curve ($M_i$) shown in FIG. 10(c). Afterwards, we extracted zero-crossing points of $M_i$ to detect the edge of each line, as indicated by circles in FIG. 10(c). Then we calculated widths of the lines, their mean and standard deviation (STD). The ratio between STD and mean of the width was 0.025, which indicates that our method effectively removed artifacts induced by non-constant manual scanning speed. In comparison, in FIG. 10(d), we show the image obtained from manual scan, but without correction using cross-correlation. Artifacts due to non-uniform scanning speed are clearly visible in FIG. 10(d).

Figure 11:
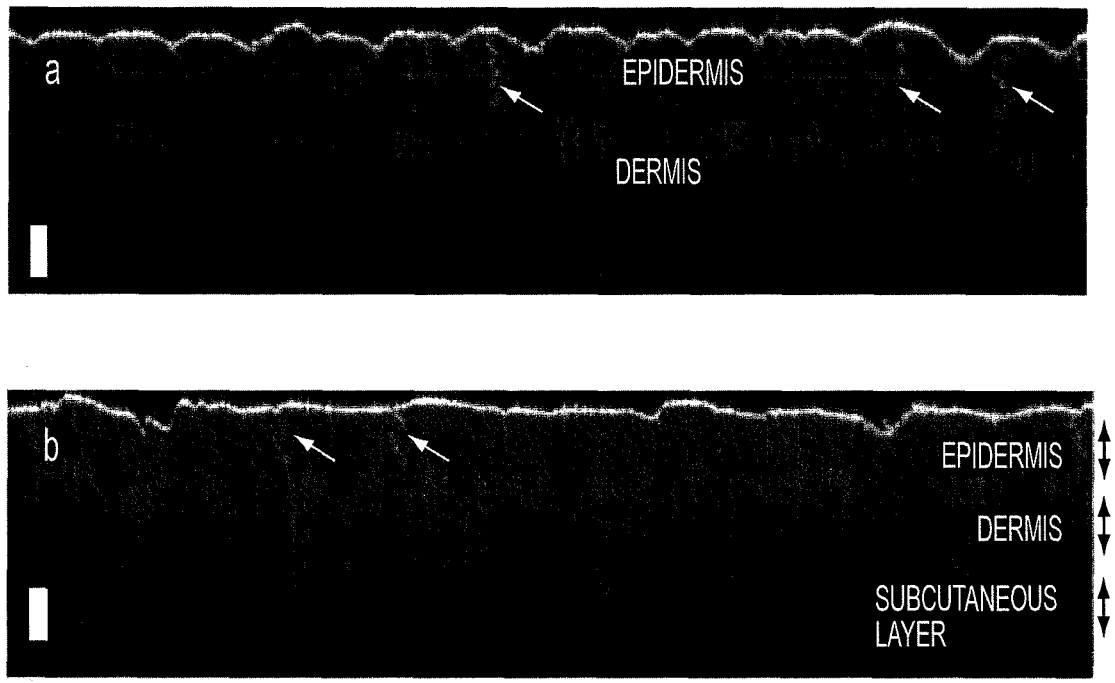
FIGS. 11A-B show manually scanned OCT image of human skin from fingertip (a) and palm (b).

We have also manually scanned the skin of a healthy volunteer using our hand-held OCT probe with 2 μm digital sampling interval. To perform manual scan, one of the author held the probe almost perpendicular to the sample surface and moved the probe laterally. Images obtained from the index finger tip and the palm are shown in FIGS. 11 (a) and (b), respectively. White scale bars in FIG. 11 represent 100 μm and arrows indicate sweat duct. Epidermis and dermis layer can be visualized in FIG. 11. As light can penetrate deeper in the palm skin, the subcutaneous layer can also be seen in FIG. 11 (b).

Figure 12:
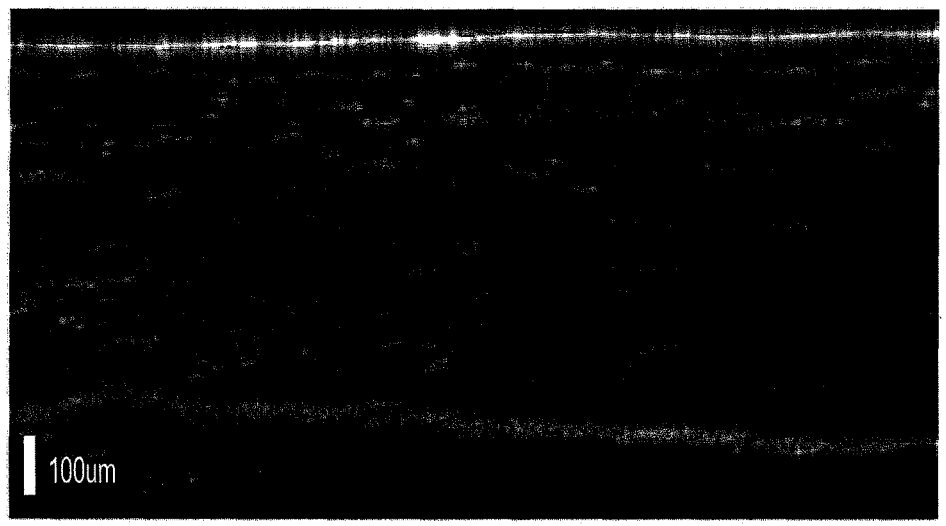
FIG. 12 shows an image of onion cells obtained from manual scanning.

To further demonstrate the effectiveness of our method on heterogeneous samples, we performed manual scan on an onion sample and show the obtained image as FIG. 12 in which hexagon shaped onion cells can be observed.

Discussion

Eq. (7) forms the mathematical foundation of this work. In deriving Eq. (7), it assumes that the speckle is fully developed. Therefore, to validate Eq. (7) experimentally, we used several different models to test our method. We used a multi-layered phantom without much heterogeneity in lateral dimension for our calibration experiments. However, most OCT images using real specimens have partially developed speckle instead of fully developed speckle. If the sample is heterogeneous, the correlation coefficient between adjacent A-scans not only depends on the lateral interval, but also depends on sample structure. Moreover, when the probe scans across a boundary within the sample, due to the abrupt change in OCT signal, a new A-scan will be attached to the data set regardless of the lateral displacement between the current and previous A-scans. As a result, heterogeneous sample can cause inaccuracy in lateral motion correction of our method. However, for highly scattering samples such as skin, it is usually reasonable to assume that areas corresponding to sample boundary take only a few pixels and therefore do not contribute significantly in the calculation of XCC. As a result, Eq. (7) is valid for highly scattering specimens when a significant portion of the specimen contains homogeneous scatterers, although speckle does not develop fully in most biological specimens. This was verified in the experiment using a quality resolution chart with abrupt changes in lateral features as a sample. We further tested and verified the method using in-situ tissue imaging.

As indicated by Eq. (7), to quantitatively estimate $\Delta x$ from XCC, it requires that we know $w_0$, the Gaussian beam waist of probing beam which can be calculated or experimentally measured. As a result, the calibrating decorrelation curve shown in FIG. 6(b) is only valid for an OCT system with a certain $w_0$. If $w_0$ used in the calculation for lateral interval between adjacent A-scans is different from the actual beam size, the image reconstructed from our algorithm will be different from the "true" image by a scaling factor in the lateral dimension. However, under such circumstances, uniform sampling can still be achieved to obtain an image that is easy for human to comprehend. In fact, the size of the imaging beam from the probe changes as the beam propagates, and the lateral PSF of OCT system depends on the image depth. Therefore, the speckle decorrelation curve has depth dependency as well. Considering the overall effect, the lateral resolution defined by the Gaussian beam waist is always slightly different from the decorrelation length of OCT signal. Moreover, To reduce the effect of the diverging beam, we took only part of an A-scan to calculate XCC when implementing our software. As a result, the statistics of different pixels within the segment of an A-scan does not vary significantly.

In this work, our assumption is that the manual scan is one dimensional in x axis and that there is no axial motion from the scanning probe, which is not exactly true in a realistic scenario. For example, human hands suffer from physiological tremor and this makes the probe to move randomly in both lateral and axial directions. However, experimental results have shown that the tremor during retinal microsurgery has low frequency motion (<1 Hz) with amplitude in the order of 100 μm [26]. As a result, with high data acquisition rate, adjacent A-scans usually do not have offset in axial direction for more than a few pixels. Moreover, a cross-correlation maximization-based shift correction algorithm was recently proposed to suppress artifact due to axial motion [27], which might be helpful to improve the performance of our image acquisition algorithm in the future. In our future study, we are going to conduct a more comprehensive theoretical and experimental study on motion tracking using OCT speckle texture analysis, by considering different types of motion including axial translation, lateral translation and rotation.

REFERENCES

1. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," *Science* 254, 1178-1181 (1991).
2. A. M. Zysk, F. T. Nguyen, A. L. Oldenburg, D. L. Marks, and S. A. Boppart, "Optical coherence tomography: a review of clinical development from bench to bedside," *J. Biomed. Opt* 12, 051403-051421 (2007).
3. S. A. Boppart, B. E. Bouma, C. Pitris, G. J. Tearney, J. G. Fujimoto, and M. E. Brezinski, "Forward-imaging instruments for optical coherence tomography," *Opt. Lett.* 22, 1618-1620 (1997).
4. X. Li, C. Chudoba, T. Ko, C. Pitris, and J. G. Fujimoto, "Imaging needle for optical coherence tomography," *Opt. Lett.* 25, 1520-1522 (2000).
5. J. Wu, M. Conry, C. Gu, F. Wang, Z. Yaqoob, and C. Yang, "Paried-angle-rotation scanning optical coherence tomography forward-imaging probe," *Opt. Lett.* 31, 1265-1267 (2006).
6. S. Han, M. V. Sarunic, J. Wu, M. Humayun, and C. Yang, "Handheld forward-imaging needle endoscope for ophthalmic optical coherence tomography inspection," *J. Biomed. Opt* 13, 020505 (2008).
7. J. Han, M. Balicki, K. Zhang, X. Liu, J. Handa, R. Taylor, and J. U. Kang, "Common-path Fourier-domain optical coherence tomography with a fiber optic probe integrated Into a surgical needle," *Proceedings of CLEO Conference* (2009).
8. M. Balicki, J. Han, I. Iordachita, P. Gehlbach, J. Handa, J. U. Kang, and R. Taylor, "Single fiber optical coherence tomography microsurgical instruments for computer and robot-assisted retinal surgery," *Proceedings of the MICCAI Conference*, London, 108-115 (2009).

9. J. Ren, J. Wu, E. J. McDowell, and C. Yang, "Manual-scanning optical coherence tomography probe based on position tracking," *Opt. Lett.* 34, 3400-3402 (2009).
10. L. Huo, J. Xi, Y. Wu, and X. Li, "Forward-viewing resonant fiber-optic scanning endoscope of appropriate scanning speed for 3D OCT imaging," *Opt. Express* 18, 14375-14384 (2010).
11. W. G. Jung, J. Zhang, L. Wang, P. Wilder-Smith, Z. P. Chen, D. T. McCormick, and N. C. Tien, "Three-dimensional optical coherence tomography employing a 2-axis microelectromechanical scanning mirror," *IEEE J. Sel. Top. Quantum Electron.* 11, 806-810 (2005).
12. J.-F. Chen, J. B. Fowlkes, P. L. Carson, and J. M. Rubin, "Determination of scan-plane motion using speckle decorrelation: Theoretical considerations and initial test," *Int J Imaging Syst Technol* 8, 38-44 (1997).
13. P. C. Li, C. J. Cheng, and C. K. Yeh, "On velocity estimation using speckle decorrelation," *IEEE Trans. Ultrason. Ferroelectr. Freq. Control* 48, 1084-1091 (2001).
14. A. Ahmad, S. G. Adie, E. J. Chaney, U. Sharma, and S. A. Boppart, "Cross-correlation-based image acquisition technique for manually-scanned optical coherence tomography," *Opt. Express* 17, 8125-8136 (2009).
15. K. Zhang, W. Wang, J. Han, and J. U. Kang, "A surface topology and motion compensation system for microsurgery guidance and intervention based on common-path optical coherence tomography," *IEEE Trans. Biomed. Eng.* 56(9), 2318-2321 (2009).
16. J. K. Barton, and S. Stromski, "Flow measurement without phase information in optical coherence tomography images," *Opt. Express* 13, 5234-5239 (2005).
17. B. Lau, R. A. McLaughlin, A. Curatolo, R. W. Kirk, D. K. Gerstmann, and D. D. Sampson, "Imaging true 3D endoscopic anatomy by incorporating magnetic tracking with optical coherence tomography: proof-of-principle for airways," *Opt. Express* 18, 27173-27180 (2010).
18. J. M. Schmitt, S. H. Xiang, and K. M. Yung, "Speckle in optical coherence tomography," *J. Biomed. Opt.* 4, 95-105 (1999).
19. J. W. Goodman, *Statistical Optics* (Wiley, 1985).
20. A. Yariv, *Optical Electronics in Modern Communications* (Oxford U. Press, 1991).
21. Y. Liu, Y. Liang, G. Mu, and X. Zhu, "Deconvolution methods for image deblurring in optical coherence tomography," *J. Opt. Soc. Am. A* 26, 72-77 (2009).
22. P. D. Woolliams, R. A. Ferguson, C. Hart, A. Grimwood, and P. H. Tomlins, "Spatially deconvolved optical coherence tomography," *Appl. Opt* 49(11), 2014-2021 (2010).
23. K. Zhang and J. U. Kang, "Graphics processing unit accelerated non-uniform fast Fourier transform for ultra-high-speed, real-time Fourier-domain OCT," *Opt. Express* 18, 23472-23487 (2010).
24. X. Li, J. Han, X. Liu, and J. U. Kang, "SNR Analysis of all-fiber common-path optical coherence tomography," *Appl. Opt.* 47, 4833-4840 (2008).
25. X. Liu and J. U. Kang, "Progress toward inexpensive endoscopic high-resolution common-path OCT", *Proc. SPIE* 7559, 755902 (2010).
26. S. Sinch and C. Riviere, "Physiological tremor amplitude during retinal microsurgery," *Proc. 28th IEEE Northeast Bioeng. Conf,* 171-172 (2002).
27. J. Lee, V. Srinivasan, H. Radhakrishnan, and D. A. Boas, "Motion correction for phase-resolved dynamic optical coherence tomography imaging of rodent cerebral cortex," *Opt. Express* 19, 21258-21270 (2011).
28. J. U. Kang, J. Han, X. Liu, K. Zhang, C. Song, and P. Gehlbach, "Endoscopic functional Fourier domain common path optical coherence tomography for microsurgery," *IEEE J. of Select. Topic in Quantum. Electron.* 16, 781-792 (2010).
29. R. F. Wagner, M. F. Insana, and D. G. Brown, "Statistical properties of radio-frequency and envelope-detected signals with applications to medical ultrasound," *J. Opt. Soc. Am. A* 4, 910-922 (1987).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A lateral-distortion corrected optical coherence tomography system, comprising:
   an optical coherence tomography sensor;
   a light source;
   a fiber-optic system optically coupled to said light source and said optical coherence tomography sensor, said fiber-optic system arranged to provide a reference beam and an observation beam;
   an optical detection system arranged to receive combined light from said reference beam and said observation beam, said optical detection system providing detection signals; and
   a data processing system arranged to communicate with said optical detection system and receive said detection signals,
   wherein said data processing system is configured to:
      construct a plurality of A-scans from said detection signals;
      calculate a cross-correlation between adjacent A-scans of said plurality of A-scans;
      calculate a displacement between adjacent A-scans of said plurality of A-scans based on said cross-correlation between adjacent A-scans;
      add said calculated displacement between each of said adjacent A-scans to determine a total distance between a first A-scan and a last A-scan of said plurality of A-scans;
      divide said total distance by a preselected sampling interval to determine a plurality of spatial positions;
      interpolate said plurality of A-scans to obtain an A-scan corresponding to each of said plurality of spatial positions; and
      assemble an image from said plurality of interpolated A-scans.

2. The lateral-distortion corrected optical coherence tomography system of claim 1, wherein the displacement between adjacent A-scans of said constructed plurality of A-scans is non-uniform due to a variance in a scanning speed of said optical coherence tomography sensor.

3. The lateral-distortion corrected optical coherence tomography system of claim 1, wherein said data processing system is configured to calculate said displacement between adjacent A-scans using the formula $$\Delta x = w_0 \sqrt{\ln\left(\frac{1}{\rho}\right)}$$

where $\Delta x$ is said displacement, $\rho$ is said cross-correlation, and $w_o$ is a beam waist of said observation beam.

4. The lateral-distortion corrected optical coherence tomography system of claim 1, wherein said cross-correlation is a Pearson cross-correlation coefficient.

5. The lateral-distortion corrected optical coherence tomography system of claim 1, wherein said data processing system is configured to calculate said cross-correlation using the formula $$\rho_{j,j+1} = \frac{\sum_{i=i_f}^{i_l}(I_{ij} - \langle I_j \rangle)(I_{i(j+1)} - \langle I_{(j+1)} \rangle)}{\sqrt{\left[\sum_{i=i_f}^{i_l}(I_{ij} - \langle I_j \rangle)^2\right]\left[\sum_{i=i_f}^{i_l}(I_{i(j+1)} - \langle I_{(j+1)} \rangle)^2\right]}}$$

where I is an intensity of an OCT signal, i is an index of a pixel in an A-scan, and j is an index of an A-scan.

6. The lateral-distortion corrected optical coherence tomography system of claim 1, wherein said spatial positions are separated by a uniform displacement.

7. A method for lateral-distortion correction in optical coherence tomography, comprising:
    receiving optical coherence tomography signals corresponding to a scanning path;
    constructing a plurality of A-scans from said optical coherence tomography signals;
    calculating a cross-correlation between adjacent A-scans of said plurality of A-scans;
    calculating a displacement between adjacent A-scans of said plurality of A-scans based on said cross-correlation between adjacent A-scans;
    adding said calculated displacement between each of said adjacent A-scans to determine a total distance between a first A-scan and a last A-scan of said plurality of A-scans;
    dividing said total distance by a preselected sampling interval to determine a plurality of spatial positions;
    interpolating said plurality of A-scans to obtain an A-scan corresponding to each of said plurality of spatial positions; and
    assembling an image from said plurality of interpolated A-scans.

8. The method for lateral-distortion correction in optical coherence tomography of claim 7, wherein the displacement between adjacent A-scans of said plurality of A-scans is non-uniform due to a variance in a scanning speed of an optical coherence tomography sensor used to generate said optical coherence tomography signals.

9. The method for lateral-distortion correction in optical coherence tomography of claim 7, further comprising calculating said displacement between adjacent A-scans using the formula $$\Delta x = w_0 \sqrt{\ln\left(\frac{1}{\rho}\right)}$$

where $\Delta x$ is said displacement, $\rho$ is said cross-correlation, and $w_o$ is a beam waist of an observation beam.

10. The method for lateral-distortion correction in optical coherence tomography of claim 7, wherein said cross-correlation is a Pearson cross-correlation coefficient.

11. The method for lateral-distortion correction in optical coherence tomography of claim 7, further comprising calculating the cross-correlation using the formula $$\rho_{j,j+1} = \frac{\sum_{i=i_f}^{i_l}(I_{ij} - \langle I_j \rangle)(I_{i(j+1)} - \langle I_{(j+1)} \rangle)}{\sqrt{\left[\sum_{i=i_f}^{i_l}(I_{ij} - \langle I_j \rangle)^2\right]\left[\sum_{i=i_f}^{i_l}(I_{i(j+1)} - \langle I_{(j+1)} \rangle)^2\right]}}$$

where I is an intensity of an OCT signal, i is an index of a pixel in an A-scan, and j is an index of an A-scan.

12. The method for lateral-distortion correction in optical coherence tomography of claim 7, wherein said spatial positions are separated by a uniform displacement.

* * * * *